(12) United States Patent
Semkiv et al.

(10) Patent No.: US 9,885,062 B2
(45) Date of Patent: Feb. 6, 2018

(54) **ETHANOL YIELD WITH REDUCTION OF BIOMASS ACCUMULATION IN THE RECOMBINANT STRAIN OF *SACCHAROMYCES CEREVISIAE* OVEREXPRESSING ALKALINE PHOSPHATE**

(71) Applicants: Institute of Cell Biology, Lviv (UA); Archer Daniels Midland Company, Decatur, IL (US)

(72) Inventors: Marta Semkiv, Lviv (UA); Kostyantyn Dmytruk, Lviv (UA); Andriy Sibirny, Lviv (UA)

(73) Assignee: Archer-Daniels-Midland Company, Decatur, IL (US)

( * ) Notice: Subject to any disclaimer, the term of this patent is extended or adjusted under 35 U.S.C. 154(b) by 70 days.

(21) Appl. No.: 14/652,133

(22) PCT Filed: Dec. 20, 2013

(86) PCT No.: PCT/US2013/076773
§ 371 (c)(1),
(2) Date: Jun. 15, 2015

(87) PCT Pub. No.: WO2014/100526
PCT Pub. Date: Jun. 26, 2014

(65) Prior Publication Data
US 2015/0322461 A1  Nov. 12, 2015

Related U.S. Application Data

(60) Provisional application No. 61/739,904, filed on Dec. 20, 2012.

(51) Int. Cl.
C12P 7/06 (2006.01)
C12N 9/16 (2006.01)

(52) U.S. Cl.
CPC ............. *C12P 7/06* (2013.01); *C12N 9/16* (2013.01); *C12Y 301/03001* (2013.01); *Y02E 50/16* (2013.01); *Y02E 50/17* (2013.01)

(58) Field of Classification Search
CPC ........................................................ C12N 9/16
See application file for complete search history.

(56) References Cited

PUBLICATIONS

Barbaric et al., "Activation of the weakly regulated PHO8 promoter in *S.cerevisiae*: chromatin transition and binding sites for the positive regulatory protein PHO4", Nucleic Acids Research, 1992, vol. 20, No. 5 1031 -1038.*
Piper et al., "The Membrane Protein Alkaline Phosphatase Is Delivered to the Vacuole by a Route That Is Distinct from the VPS-dependent Pathway", The Journal of Cell Biology, vol. 138, No. 3, Aug. 11, 1997 531-545.*
Qiao et al., "Zinc status and vacuolar zinc transporters control alkaline phosphatase accumulation and activity in *Saccharomyces cerevisiae*", Mol Microbiol. Apr. 2009 ; 72(2): 320-334. doi:10.1111/j.1365-2958.2009.06644.x.*
Tuleva et al "A speci¢c alkaline phosphatase from *Saccharomyces cerevisiae* with protein phosphatase activity", FEMS Microbiology Letters 161 (1998) 139-144.*
Ni et al., "Transposon Mutagenesis to Improve the Growth of Recombinant *Saccharomyces cerevisiae* on D-Xylose", Applied and Environmental Microbiology, Apr. 2007, vol. 73, No. 7, p. 2061-2066. doi:10.1128/AEM.02564-06.*
Clontech "Yeast Protocol Handbook", Jul. 2009. Retrieved from: <http://www.google.com/url?sa=t&rct=j&q=&esrc=s&source=web &cd=1&ved=0ahUKEwjZvfGolKbQAhXrzFQKHYwmCYwQF-ggbMAA&url=http%3A%2F%2Fwww.clontech.com%2Fxxclt_ ibcGetAttachment.jsp%3FcItemId%3D17602&usg= AFQjCNFWn9PqpRF-CyAKX9dywFWOHBrx2Q &sig2=igSShdaFZ9V4wGTHtk1WhA&bym=bv.138493631,d. cGw >.*

* cited by examiner

*Primary Examiner* — Suzanne M Noakes
(74) *Attorney, Agent, or Firm* — Corey M. Crafton; Andrew F. Nilles

(57) ABSTRACT

Described herein is a method to increase ethanol yield during alcoholic fermentation by expression a truncated versions of the *Saccharomyces cerevisiae* PHO8 gene coding for vacuolar or cytosolic form of alkaline phosphatase, which expression lowers biomass accumulation while diverting greater carbon to ethanol production. Also described are as nucleic acid sequences and vectors for expression of the PHO8 gene and strains carrying the same. Strains containing intact PHO8 gene encoding vacuolar form of alkaline phosphatase, had slightly lower intracellular ATP levels with insignificant changes in biomass accumulation and up to 13% increase in ethanol production.

9 Claims, 12 Drawing Sheets

A

B

SEQUENCE LISTING

<160> NUMBER OF SEQ ID NOS: 16

<210> SEQ ID NO 1
<211> LENGTH: 43
<212> TYPE: DNA
<213> ORGANISM: Artificial Sequence
<220> FEATURE:
<223> OTHER INFORMATION: PCR Primer SM16

<400> SEQUENCE: 1
ccggaattcg acgggcagtc tgttggaata gaaatcaact atc                43

<210> SEQ ID NO 2
<211> LENGTH: 66
<212> TYPE: DNA
<213> ORGANISM: Artificial Sequence
<220> FEATURE:
<223> OTHER INFORMATION: PCR Primer SM17

<400> SEQUENCE: 2
catcatttta tatgtttata ttcatctaga cccggggtcg acttgatcct attacattat    60
caatcc                                                              66

<210> SEQ ID NO 3
<211> LENGTH: 66
<212> TYPE: DNA
<213> ORGANISM: Artificial Sequence
<220> FEATURE:
<223> OTHER INFORMATION: PCR Primer SM18

<400> SEQUENCE: 3
ggattgataa tgtaatagga tcaagtcgac cccgggtcta gatgaatata aacatataaa    60
atgatg                                                              66

<210> SEQ ID NO 4
<211> LENGTH: 42
<212> TYPE: DNA
<213> ORGANISM: Artificial Sequence
<220> FEATURE:
<223> OTHER INFORMATION: PCR Primer SM19

<400> SEQUENCE: 4
cccaagcttg acgggcagtc tgagaaatat gtgaatgttg ag                 42

<210> SEQ ID NO 5
<211> LENGTH: 30
<212> TYPE: DNA
<213> ORGANISM: Artificial Sequence
<220> FEATURE:
<223> OTHER INFORMATION: PCR Primer Ko419

<400> SEQUENCE: 5
cgcgtcgact taattaaagt ccaatgctag                               30

<210> SEQ ID NO 6
<211> LENGTH: 62
<212> TYPE: DNA
<213> ORGANISM: Artificial Sequence
<220> FEATURE:
<223> OTHER INFORMATION: PCR Primer Ko420

<400> SEQUENCE: 6
gatatcgaca aaggaaaagg ggcggccgcg gatccctcga gtgtatatga gatagttgat    60
tg                                                                  62

-continued

<210> SEQ ID NO 7
<211> LENGTH: 62
<212> TYPE: DNA
<213> ORGANISM: Artificial Sequence
<220> FEATURE:
<223> OTHER INFORMATION: PCR Primer Ko453

<400> SEQUENCE: 7
caatcaacta tctcatatac actcgaggga tccgcggccg cccctttttcc tttgtcgata    60 tc                                                                  62

<210> SEQ ID NO 8
<211> LENGTH: 29
<212> TYPE: DNA
<213> ORGANISM: Artificial Sequence
<220> FEATURE:
<223> OTHER INFORMATION: PCR Primer Ko454

<400> SEQUENCE: 8 cccccccggggg caaattaaag ccttcgagc                                    29

<210> SEQ ID NO 9
<211> LENGTH: 33
<212> TYPE: DNA
<213> ORGANISM: Artificial Sequence
<220> FEATURE:
<223> OTHER INFORMATION: PCR Primer Ko508

<400> SEQUENCE: 9
cgcggatcca tgatgactca cacattacca agc                                 33

<210> SEQ ID NO 10
<211> LENGTH: 38
<212> TYPE: DNA
<213> ORGANISM: Artificial Sequence
<220> FEATURE:
<223> OTHER INFORMATION: PCR Primer Ko509

<400> SEQUENCE: 10
tttgcggccg ctcagttggt caactcatgg tagtattc                            38

<210> SEQ ID NO 11
<211> LENGTH: 39
<212> TYPE: DNA
<213> ORGANISM: Artificial Sequence
<220> FEATURE:
<223> OTHER INFORMATION: PCR Primer SM28

<400> SEQUENCE: 11
cgcggatcca tgtctgcatc acacaagaag aagaatgtc                           39

<210> SEQ ID NO 12
<211> LENGTH: 42
<212> TYPE: DNA
<213> ORGANISM: Artificial Sequence
<220> FEATURE:
<223> OTHER INFORMATION: PCR Primer SM29

<400> SEQUENCE: 12
tttgcggccg ctcaatctga tgtgtgtttg gtgtccctaa tc                       42

<210> SEQ ID NO 13
<211> LENGTH: 87
<212> TYPE: DNA

```
<213> ORGANISM: Artificial Sequence
<220> FEATURE:
<223> OTHER INFORMATION: PCR Primer SM30

<400> SEQUENCE: 13
cgcggatcca tgtttaaatc tgttgtttat tcaattttag ccgcttcttt ggccaatgca    60
tctgcatcac acaagaagaa gaatgtc                                        87

<210> SEQ ID NO 14
<211> LENGTH: 37
<212> TYPE: DNA
<213> ORGANISM: Artificial Sequence
<220> FEATURE:
<223> OTHER INFORMATION: PCR Primer SM31

<400> SEQUENCE: 14
cgcggatcca tgagatttcc ttcaattttt actgcag                             37

<210> SEQ ID NO 15
<211> LENGTH: 51
<212> TYPE: DNA
<213> ORGANISM: Artificial Sequence
<220> FEATURE:
<223> OTHER INFORMATION: PCR Primer SM32

<400> SEQUENCE: 15
gacattcttc ttcttgtgtg atgcagactc tcttttatcc aaagatacccc c            51

<210> SEQ ID NO 16
<211> LENGTH: 51
<212> TYPE: DNA
<213> ORGANISM: Artificial Sequence
<220> FEATURE:
<223> OTHER INFORMATION: PCR Primer SM33

<400> SEQUENCE: 16
ggggtatctt tggataaaag agagtctgca tcacacaaga agaagaatgt c             51
```

ETHANOL YIELD WITH REDUCTION OF BIOMASS ACCUMULATION IN THE RECOMBINANT STRAIN OF SACCHAROMYCES CEREVISIAE OVEREXPRESSING ALKALINE PHOSPHATE

CROSS REFERENCE TO RELATED APPLICATION[S]

This application is a national phase entry of PCT application No. PCT/US2013/076773 filed on Dec. 20, 2013, which claims priority to U.S. provisional patent application No. 61/739,904 filed Dec. 20, 2012.

TECHNICAL FIELD

The invention relates to the field of ethanol; production by fermentation, and more particularly to expression of an alkaline phosphatase e gene in the yeast Saccahromyces cerevisiae to improve the production of ethanol while reducing biomass accumulation.

BACKGROUND OF THE INVENTION

Alcoholic fermentation represents the largest application of the yeast Saccahromyces cerevisiae in the field of industrial biotechnology with the production of over 80 billion liters of fuel, industrial and beverage ethanol in 2011. Over the past decade and due to economic and environmental reasons, the world has experienced exponential growth in the production of fuel ethanol (Schubert, 2006). Though lignocellulose is considered to be one of the most promising feedstocks for production of fuel ethanol, the current industrial production of fuel ethanol relies heavily on the fermentation of traditional feedstocks such as sucrose (derived primarily from sugarcane or sweet sugar beets) and glucose obtained from starchy materials (corn, wheat, barley, potatoes etc). The most common organism currently used for bioethanol production is the baker's yeast, Saccharomyces cerevisiae. This yeast catabolizes glucose via the glycolytic Embeden Meyerhof Pathway (EMP) pathway yielding 2 moles ATP per mole of consumed glucose. The efficiency of this pathway in yeast is low with a maximal biomass yield of around 7% and an ethanol yield in the range 90 and 93% of the theoretical value (Ingledew, 1999). However, at industrial scale the 7% of the sugar that is converted to cell mass represents a huge amount of by-product, which though valuable as animal feed significantly lowers the overall yield of the target product, ethanol. Even a slight improvement in ethanol yield by S. cerevisiae, can add several millions 1 liters of ethanol to the worldwide production of ethanol production annually.

In contrast to S. cerevisiae, the bacterium Zymomonas mobilis ferments glucose through Entner Doudorf (ED) pathway. This pathway gives only 1 mole of ATP per mole of glucose, and directs only 3% of glucose to cell biomass achieving ethanol yield of up to 97% of the possible theoretical value (Sprenger, 1996). This indicates that lowering the level of ATP yield during alcoholic fermentation increases ethanol yield with reduced substrate conversion to cell mass. Furthermore, Z. mobilis has another important advantage over S. cerevisiae: in faster fermentation of glucose to ethanol (Sprenger, 1996, Panesar et al., 2006). The higher productivity of Z. mobilis is frequently attributed to faster rate of sugar uptake and subsequent catabolism rather than low ATP yield. Attempts to substitute S. cerevisiae by Z. mobilis for the production of industrial ethanol were considered to increase ethanol yield by 3-4% thereby adding several hundred million liters worldwide annually. However, Z. mobilis has several serious drawbacks which hamper its industrial use and these consist of: (i) a very narrow substrate range (sucrose is hardly fermented with low yield), (ii) natural auxotrophy for lysine, methionine and some vitamins, (iii) non-GRAS status, which prevents use of biomass as feed additive, (iv) requirement for a higher pH to grow (Jeffries, 2005; Bai et al., 2008; Abbas, unpublished finding). Furthermore, the technology of yeast cell utilization for alcoholic fermentation is well developed whereas the use of bacterial cells for ethanol production is far less common. Thus, a better approach to increase ethanol yield and reduce cell mass production is to construct yeast strains which yield less ATP during alcoholic fermentation (e.g. one mole ATP, as Z. mobilis does in ED pathway). These new yeast strains would combine all of the possible advantages of yeast with the high ethanol yield of Z. mobilis. There are several approaches that can be used to achieve this goal, for example: substitution of EMP pathway in yeast by ED pathway from Z. mobilis or other bacteria possessing genes of the pathway; increasing the activity of enzymes involved in generation of futile cycles; construction of recombinant strains with elevated ATPase activity; and the introduction of heterologous genes encoding for plasma membrane symporters.

The first approach tried was to express ED dehydratase and ED aldolase genes edd and eda in a phosphofructokinase deficient mutant of S. cerevisiae (Lancashire et al., 1998). The yeast transformants obtained grew and fermented glucose to ethanol, though activities of ED dehydratase and ED aldolase were not measured. The work described in this patented work, was not further developed as there is no additional reports in the scientific literature. Quite often prokaryotic enzymes display low or no activity in S. cerevisiae hosts (Hahn-Hagerdal et al., 2007). This is probably due in part to improper folding or instability of the expressed bacterial protein products in yeast. In addition, there are difficulties in NADP regeneration in the yeast engineered ED pathway as NADPH produced in glucose-6-phosphate dehydrogenase reaction, cannot be reoxidized via alcohol dehydrogenase reaction. It has already been reported that the major alcohol dehydrogenases in S. cerevisiae utilize NADH but not NADPH and yeast does not possess NADH/NADPH transhydrogenase (Lescovac et al., 2002; Jeffries and Jin, 2004). In order to maintain a low level of ATP during yeast alcoholic fermentation through EMP pathway, it is not necessary to substitute it for a pathway with lower efficiency. A better approach to achieve the above is to keep EMP pathway unchanged and to lower level of ATP by a more specific approaches that rely on the activation of some cytosolic ATPase or via the induction or construction of some kind of futile cycle to dissipate cellular pool of ATP.

In our previous work, we carried out a successful attempt to decrease intracellular ATP level by overexpression of 5' part of the S. cerevisiae SSB1 gene encoding cytosolic ATPase domain and by the heterologous gene apy encoding apyrase from Escherichia coli (Sibirny et al., 2010). Some of the constructed strains showed a decrease in cellular ATP level during anaerobic, aerobic or semi-anaerobic cultivation and were characterized by a reduction in cellular biomass yield with the corresponding increase in ethanol yield during glucose utilization under anaerobic, aerobic or semi-anaerobic conditions. We suggested that this approach can be useful for the construction of a new generation of industrial strains of S. cerevisiae which are characterized by improved ethanol yield from conventional (glucose, sucrose) and non-conventional (lignocellulose) feedstocks.

In this application we describe another approach to lowering cellular ATP by overexpression of intact or truncated versions of the *S. cerevisiae* PHO8 gene, encoding alkaline phosphatase.

SUMMARY OF THE INVENTION

In a general embodiment, the invention provides a strain of *S. cerevisiae* comprising a nucleic acid sequence encoding an alkaline phosphatase enzyme operably linked to a promoter that expresses the alkaline phosphatase enzyme in the cell. In certain more particular embodiments. The strain of the alkaline phosphatase enzyme expressed by the nucleic acid sequence contains a vacuolar targeting sequence and the alkaline phosphatase is present in the vacuole of the cell. In other distinctive embodiments, the alkaline phosphatase enzyme lacks a vacuolar targeting sequence and alkaline phosphatase is present in the cytoplasm of the cell.

In the most useful embodiments the strain overexpresses alkaline phosphatase in the cell relative to a parent cell lacking the nucleic acid sequence encoding the alkaline phosphatase. In certain embodiments of overexpression the cell contains multiple copies of the nucleic add sequence encoding an alkaline phosphatase enzyme operably linked to a promoter that expresses the alkaline phosphatase enzyme in the cell. In some particular embodiments, be nucleic acid sequence encoding an alkaline phosphatase enzyme operably linked to a promoter that expresses the alkaline phosphatase enzyme in the cell is integrated into the genome of the cell.

In particularly useful embodiments the promoter used to overexpress the alkaline phosphatase activity is an ethanol inducible promoter from *S. cerevisiae*. In exemplary embodiments, the inducible promoter is an alcohol dehydrogenase promoter.

The embodiments of the most useful strains are characterized by producing a higher titer of ethanol during an anaerobic fermentation period than a parent strain lacking the nucleic acid sequence encoding the alkaline phosphatase enzyme operably linked to a promoter that expresses the alkaline phosphatase enzyme. Also, the most useful strains are further characterized by having a reduced biomass accumulation rate during an anaerobic fermentation period than a parent strain lacking the nucleic acid sequence encoding the alkaline phosphatase enzyme operably linked to a promoter that expresses the alkaline phosphatase enzyme.

In a related aspect there is provided a method of producing ethanol comprising growing at least one of the forging strains under anaerobic growth conditions for a time sufficient to produce ethanol.

DETAILED DESCRIPTION OF THE INVENTION

Strains, Plasmids and Growth Conditions

Figure 1:
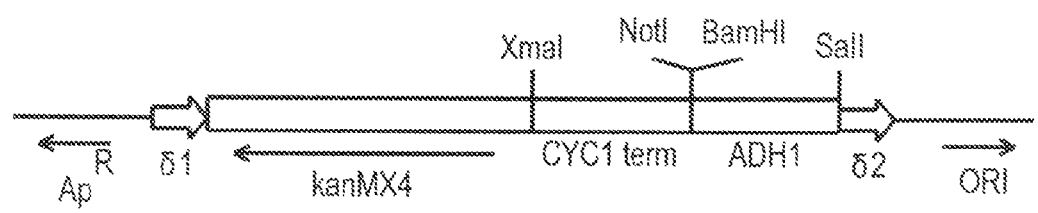
FIG. 1. The linear schemes of plasmids pUC57-delta1_2-ADHpr-CYCt-kanMX (A), pUC57-delta1_2-ADHpr-PHO8-CYCt-kanMX (B). δ1, δ2—δ elements—long terminal repeats of yeast retrotransposon Ty1; ADH1 pr—promoter of the gene encoding alcohol dehydrogenase; CYC1 term—terminator of cytochrome C gene; kanMX4—gene providing resistance to the antibiotic geneticin; PHO8—intact ORF encoding alkaline phosphatase.
Figure 1:
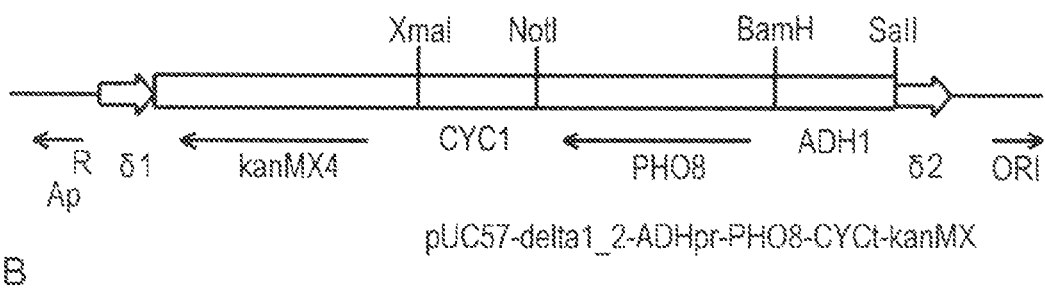

The *Saccharomyces cerevisiae* strain BY4742 (MATα, his3Δ1, leu2Δ0, lys2Δ0, ura3Δ0; (Giaever et al., 2002) and an industrial strain designated AS400 were used for the expression of the intact or truncated versions of PHO8 ORF coding for the alkaline phosphatase, *Escherichia coli* DH5α (Φ80dlacZΔM15, recA1, endA1, gyrA96, thi-1, hsdR17 ($r_K^+$, $m_K^+$), supE44, relA1, deoR, Δ(lacZYA-argF) U169) was used for general purposes and routine subcloning.

For the isolation of plasmid DNA *E. coli* strains were grown in LB media at 37° C. for 18 hours as described (Sambrook and Rusell 2001). *S. cerevisiae* strains were incubated at 30° C. For routine application, yeast strains were maintained in a rich YPD medium (1% yeast extract, 1% peptone and 2% glucose) or in a minimal medium of YNB (0.67%, yeast nitrogen base without amino acids, DIFCO, 0.5% ammonium sulfate, 2% glucose) media. For ethanol fermentation, YNB medium was supplemented with 10% glucose or Corn Steep Liqour (CSL) medium supplemented with hydrolyzed corn maltodextrin were used. When antibiotic selection was needed, strains were incubated with ampicillin (100 μg ml$^{-1}$) or geneticin (200 mg L$^{-1}$). When required, histidine (20 mg L$^{-1}$), leucine (60 mg L$^{-1}$), lysine (20 mg L$^{-1}$), or uracil (20 mg L$^{-1}$) were added. Chromogenic substrates X-gal and IPTG (Fermentas, Vilnius, Lithuania) were used according to the manufacturer specifications.

DNA Manipulations.

Genomic DNA from *S. cerevisiae* strains was isolated using the Wizard® Genomic DNA Purification Kit (Promega, Madison, Wis. USA). Plasmid DNA from *E. coli* was isolated using the Wizard® Plus SV Minipreps DNA Purification System (Promega). Taq and High Fidelity polymerase mix, T4 DNA ligase, T4 DNA polymerase and restriction enzymes were used according to recommendation of supplier (Fermentas). *S. cerevisiae* transformation was performed by standard protocol (Sambrook and Russell 2001).

Construction of Plasmids.

Expression Cassette Preparation.

154 bp part of *S. cerevisiae* YJRWdelta12 sequence was amplified from genomic DNA of *S. cerevisiae* strain BY4742 using the primers

```
SM16 (CCG GAA TTC GAC GGG CAG TCT GTT GGA

ATA GAA ATC AAC TAT C)
and

SM17 (CAT CAT TTT ATA TGT TTA TAT TCA TCT

AGA CCC GGG GTC GAC TTG ATC CTA TTA CAT

TAT CAA TCC)
``` and the other 180 bp part of this sequence was amplified from the same template using the primers

```
SM18 (GGA TTG ATA ATG TAA TAG GAT CAA GTC

GAC CCC GGG TCT AGA TGA ATA TAA ACA TAT

AAA ATG ATG)
and

SM19 (CCC AAG CTT GAC GGG CAG TCT GAG AAA

TAT GTG AAT GTT GAG).
```

Then these two parts containing delta sequences were fused via overlap PCR using primers SM16 and SM19, digested with EcoRI and HindIII and cloned into EcoRI/HindIII-linearized plasmid pUC57. The resulted plasmid was named pUC57-delta1_2, 807 bp DNA fragment corresponding to ADH1 gene (encoding alcohol dehydrogenase) promoter was amplified from genomic DNA of *S. cerevisiae* strain BY4742 using primers

```
Ko419 (CGC GTC GAC TTA ATT AAA GTC CAA TGC

TAG)
and

Ko420 (GAT ATC GAC AAA GGA AAA GGG GCG GCC

GCG GAT CCC TCG AGT GTA TAT GAG ATA GTT GAT

TG).
```

A 269 bp DNA fragment corresponding to CYC1 gene (encoding cytochrome C) terminator was amplified from genomic DNA of BY4742 strain using primers

```
Ko453 (CAA TCA ACT ATC TCA TAT ACA CTC GAG

GGA TCC GCG GCC GCC CCT TTT CCT TTG TCG ATA

TC)
and

Ko454 (CCC CCC GGG GCA AAT TAA AGC CTT CGA

GC).
```

Then promoter and terminator were fused via overlap PCR using printers Ko419 and Ko454. The obtained DNA fragment was digested with SalI and XmaI endonucleases and cloned into corresponding sites of the plasmid pUC57-delta1_2 giving the plasmid pUC57-delta1_2-ADHpr-CYCt. A 1470 bp DNA fragment corresponding to the selective marker kanMX providing resistance to geneticin was cut out from the plasmid pRS303K with restriction endonucleases SacI and SmaI, blunt-ended and cloned into XbaI-digested and blunted plasmid pUC57-delta1_2-ADHpr-CYCt yielding the plasmid pUC57-delta1_2-ADHpr-CYCt-kanMX (FIG. 1A).

Plasmid for PHO8 Expression.

A 1701 bp DNA fragment bearing the ORF of PHO8 gene coding for unspecific alkaline phosphatase was amplified from genomic DNA of *S. cerevisiae* strain BY4742 using primers

```
Ko508 (CGC GGA TCC ATG ATG ACT CAC ACA TTA

CCA AGC)
and

Ko509 (TTT GCG GCC GCT CAG TTG GTC AAC TCA

TGG TAG TAT TC).
```

This fragment was digested with BamHI and NotI and subcloned into BamHI/NotI digested plasmid pUC57-delta1_2-ADHpr-CYCt-kanMX. The resulted plasmid was designated pUC57-delta1_2-ADHpr-PHO8-CYCt-kanMX (FIG. 1B).

Plasmids for Truncated Versions of PHO8 Gene Expression.

It was decided to create several truncated forms of alkaline phosphatase. The first form lacks the 60 initial amino acids that are responsible for transmembrane protein delivery; and 22 terminal amino acids, that compose the C-terminal propeptide that is normally cleaved from the protein in vacuole. A 1452 bp DNA fragment corresponding to this truncated form, was amplified from genomic DNA of BY4742 strain using primers

SM28 (CGC GGA TCC ATG TCT GCA TCA CAC AAG

AAG AAG AAT GTC)
and

SM29 (TTT GCG GCC GCT CAA TCT GAT GTG TGT

Figure 2:
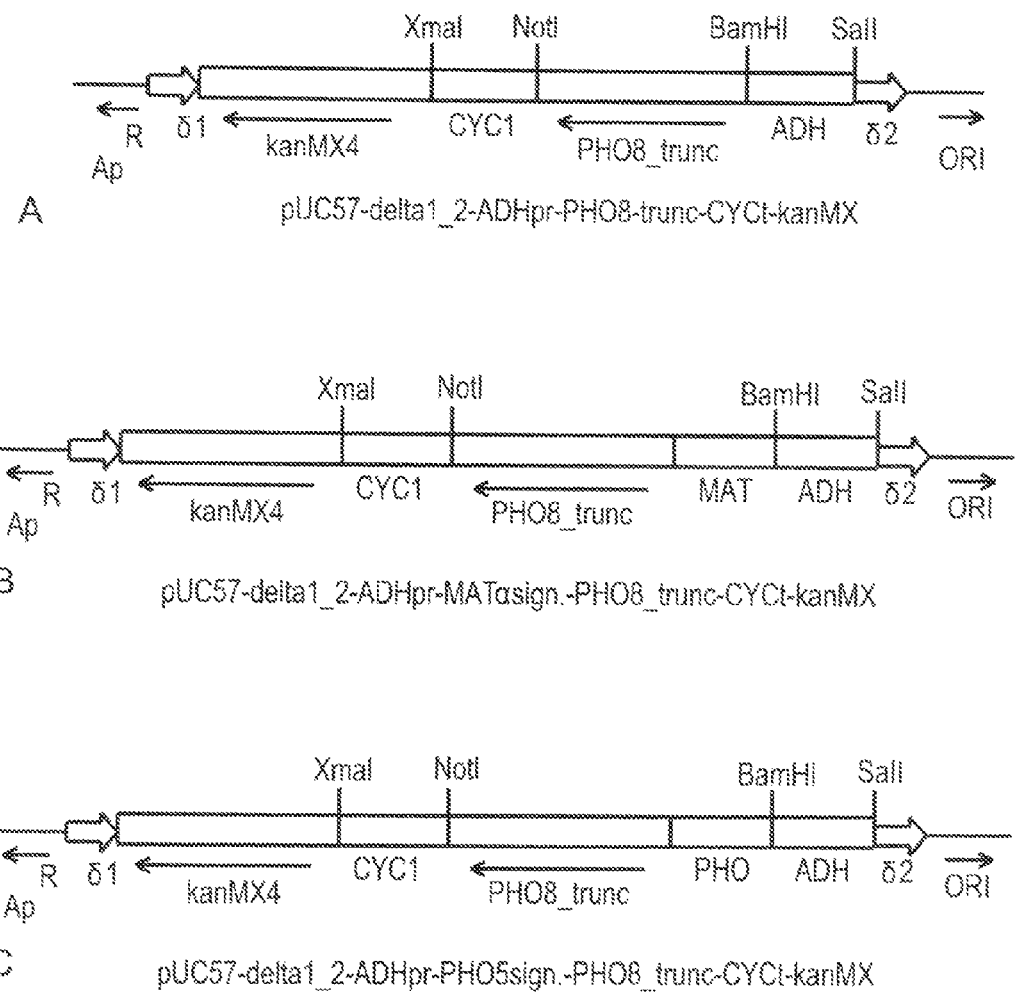
FIG. 2. The linear schemes of plasmids pUC57-delta1_2-ADHpr-PHO8_trunc-CYCt-kanMX (A), pUC57-delta1_2-ADHpr-MATαsign.-PHO8_trunc-CYCt-kanMX (B), pUC57-delta1_2-ADHpr-PHO5sign.-PHO8_trunc-CYCt-kanMX (C). PHO8_trunc—gene encoding truncated form or alkaline phosphatase that lacks 60 initial amino acids that are responsible for transmembrane protein delivery; and 22 terminal amino acids, that consist of the C-terminal propeptide that is normally cleaved from the protein in cellular vacuoles; MATαsign.-PHO8_trunc—gene encoding truncated form of alkaline phosphatase that has extracellular export signal from mating pheromone a-factor (MF1α) instead of its natural delivery signal; PHO5sign.-PHO8_trunc—gene encoding truncated form of alkaline phosphatase that has extracellular export signal from acid phosphatase (PHO5).

TTG GTG TCC CTA ATC), digested with endonucleases BamHI and NotI and cloned into BamHI/NotI digested plasmid pUC57-delta1_2-ADHpr-PHO8-CYCt-kanMX. The obtained plasmid was designated pUC57-delta1_2-ADHpr-PHO8_trunc-CYCt-kanMX (FIG. 2A). The second form of alkaline phosphatase was constructed that has extracellular export signal from mating pheromone a-factor (MF1α) instead of its natural delivery signal. To construct such a form, the 258 bp DNA fragment corresponding to MF1α export signal, was amplified from genomic DNA of BY4742 strain using primers SM31 (CGC GGATCCATG AGA TTT CCT TCA ATT TTT ACT GCA G) and SM32 (GAC ATT CTT CTT CTT GTG TGA TGC AGA CTC TCT TTT ATC CAA AGA TAC CCC), and the 1452 bp DNA fragment corresponding to PHO8 truncated form, was amplified from the same template using primers

SM33 (GGG GTA TCT TTG GAT AAA AGA GAG TCT GCA

TCA CAC AAG AAG AAG AAT GTC)

and SM29. Then both fragments were fused by overlap-PCR using primers SM31/SM29, digested with endonucleases BamHI and NotI and cloned into BamHI/NotI digested plasmid pUC57-delta1_2-ADHpr-PHO8-CYCt-kanMX. The constructed plasmid was designated pUC57-delta1_2-ADHpr-MATαsign.-PHO8_trunc-CYCt-kanMX (FIG. 2B). The third form of alkaline phosphatase has the extracellular export signal from acid phosphatase (PHO5). To construct such a form, a 1503 bp DNA fragment corresponding to PHO8 truncated form was fused with PHO5 delivery signal, and amplified from genomic DNA of BY4742 strain using primers

SM30 (CGC GGATCC ATG TTT AAA TCT GTT GTT TAT

TCA ATT TTA GCC GCT TCT TTG GCC AAT GCA TCT

GCA TCA CAC AAG AAG AAG AAT GTC)
and

SM29 (TTT GCG GCC GCT CAA TCT GAT GTG TGT TTG

GTG TCC CTA ATC), digested with endonucleases BamHI and NotI and cloned into BamHI/NotI digested plasmid pUC57-delta1_2-ADHpr-PHO8-CYCt-kanMX. The Constructed plasmid was designated as pUC57-delta1_2-ADHpr-PHO5sign.-PHO8_trunc-CYCt-kanMX (FIG. 2C).

Selection of S. Cerevisiae Transformants.

The vectors containing full or truncated versions of the PHO8 gene were digested with the AhdI restriction endonuclease. After that DNA fragments containing expression cassette and selective marker flanked by two parts of delta sequences, were eluted from an agarose gel and used for transformation of S. cerevisiae strains BY4742 and AS400. The transformants were selected on a solid YPD medium supplemented with 200 mg/L of geneticin. The selected transformants were stabilized by alternating cultivation in non-selective and selective media and examined by diagnostic PCR using a forward primer specific to the ADH1 promoter (Ko419) and a reverse one specific to PHO8 gene (Ko509).

Assay of Alkaline Phosphatase and ATP in Yeast Cells.

Alkaline phophatase activity was assayed by using p-nitrophenylphosphate as the substrate with cell extracts as the enzyme source, as described elsewhere (Kaneko et al., 1982). One unit of alkaline phosphatase activity was defined as the amount of enzyme which liberates 1 μmol of p-nitrophenol per min under the assay conditions.

ATP extraction from the S. cerevisiae cells was performed using the method of metabolites extraction with boiling ethanol and subsequent evaporation (Entian et al. 1983). To optimize ATP assay via ethanol extraction, a wide range of yeast biomass from 2 to 15 mg was tested. Reproducible results were obtained during ATP extraction with 8-10 mg of S. cerevisiae cells using 1 ml of boiling ethanol. The measurement of extracted ATP level was determined using a mixture of hexokinase and glucose-6-phosphate dehydrogenase (Ano Y. et al. 2005).

Ethanol Production and Growth Analysis.

Strains were grown overnight in YPD media followed by washing of cells with sterile water and an equal amounts of each culture were used to inoculate test media. For S. cerevisiae BY4742 strain and its PHO8-expressing derivatives, YNB supplemented with 10% glucose was used. Strains were grown using a rotary shaker Inkubator 1000 Heidolph (Schwabach, Germany) under semi-anaerobic (120 revolutions/min) conditions at 30° C. and samples were taken every 24 hours. For S. cerevisiae AS400 strain and its PHO8-expressing derivatives, a Corn Steep Liquor (CSL) medium supplemented with hydrolyzed maltodextrin was used. Strains were incubated under semi-anaerobic condition at 34° C. for 2 days and samples were taken every 24 hours. Ethanol and glucose concentrations were measured by protocols described elsewhere (Gonchar et al., 2001, Gonchar, 1998).

CSL Medium Preparation.

To prepare Solution 1, 200-280 g of maltodextrin was mixed with 800 ml of water and the pH adjusted to 6.0. Alpha-amylase (at a rate of 0.1 unit of Liquizyme SC DS per grant of maltodextrin) was added for liquefaction with the mixture heated to 80° C. and sample held for 30 minutes.

To prepare Solution 2, 63 ml of CSL Concentrate (containing ~50% dry solids) was mixed with 137 ml of deionized water. Following that Solutions 1 and 2 were autoclaved, cooled, combined and mixed. An aliquot of glucoamylase (at a rate of 0.2 units of glucoamylase per gram of maltodextrin) was added to sterile flasks and the flasks were incubated at 28° C. Glucose concentration was determined before yeast inoculation.

Results

Cloning and Overexpression of Intact Form of Alkaline Phosphatase.

S. cerevisiae unspecific alkaline phosphatise, encoded by gene PHO8, catalyzes the hydrolysis of the diphosphate bonds in different compounds including ATP (Kaneko et al., 1982). Therefore this enzyme may operate as other ATPases. In order to carry out the hydrolysis of diphosphate bonds in cells The activity of this enzyme need to be quite high. The activity of this cloned enzyme in S. cerevisiae cells depends on many factors, among them strength of chosen promoter, stability of produced mRNA, absence of posttranslational enzyme inhibition, and the number of copies of the gene integrated into the host genome. We have shown that ADH1 promoter of the gene encoding alcohol dehydrogenase provides inducible expression of target genes, under the conditions of alcoholic fermentation (Sibirny et al, 2011). We decided to use this promoter for PHO8 gene expression. In order to get higher copy number of PHO8 gene integrated into the yeast genome, an integrative plasmid containing δ sequences was constructed. The S. cerevisiae δ sequences are the long terminal repeats of the retro-transposons Ty1 and Ty2. A total of approximately 425 δ sequences are typically dispersed throughout the yeast genome. It was shown that usage of δ sequences-based vectors, can provide tandem multicopy integration in one or several sites of yeast genomic DNA via homologous recombination (Lee and Da Silva, 1997). The δ sequences-based plasmid harboring PHO8 gene under the control of ADH promoter was constructed as described in Materials and Methods and subsequently transformed into S. cerevisiae laboratory strain BY4742.

Figure 3:
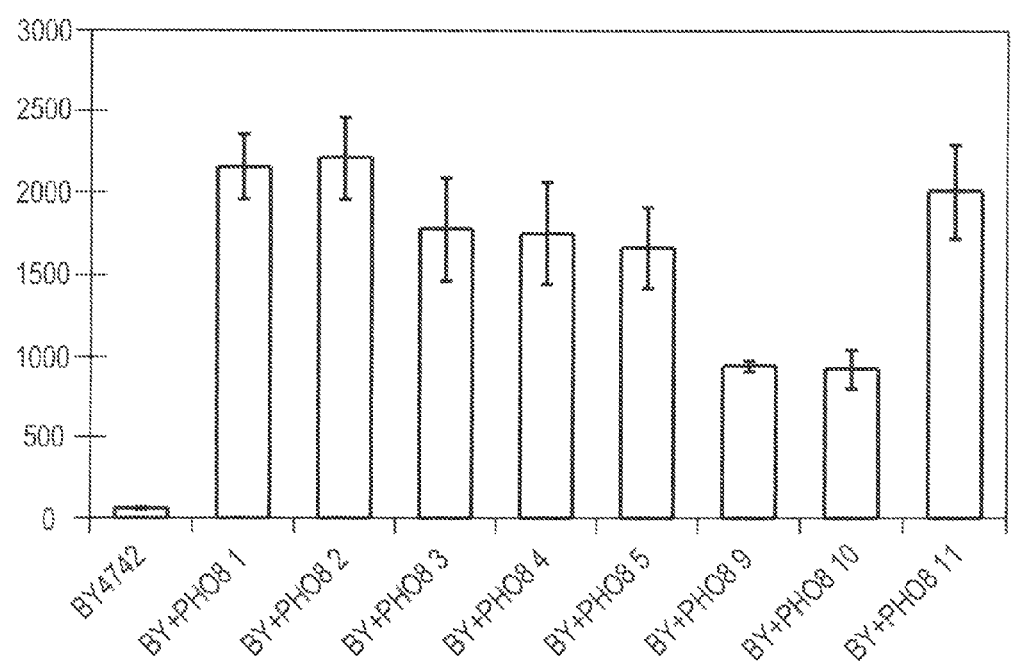
FIG. 3. Specific alkaline phosphatase activity (in nmoles of product/mg of prot.*min) of cell-free extracts of strains bearing plasmid pUC57-delta1_2-ADHpr-PHO8-CYCt-kanMX. BY4742—recipient strain.

The specific alkaline phosphatase activity of the selected recombinant strains was assayed. Among 11 tested transformants, six strains were characterized by considerably higher specific phosphatase activity (FIG. 3, strains 1-5 and 11). In these strains, the specific activity of alkaline phospatase was 30-40-fold higher when compared to the initial host strain BY4742. Thus, this constructed expression vector can be used for efficient multi-copy integration into the genome of a Saccharomyces host.

Figure 4:
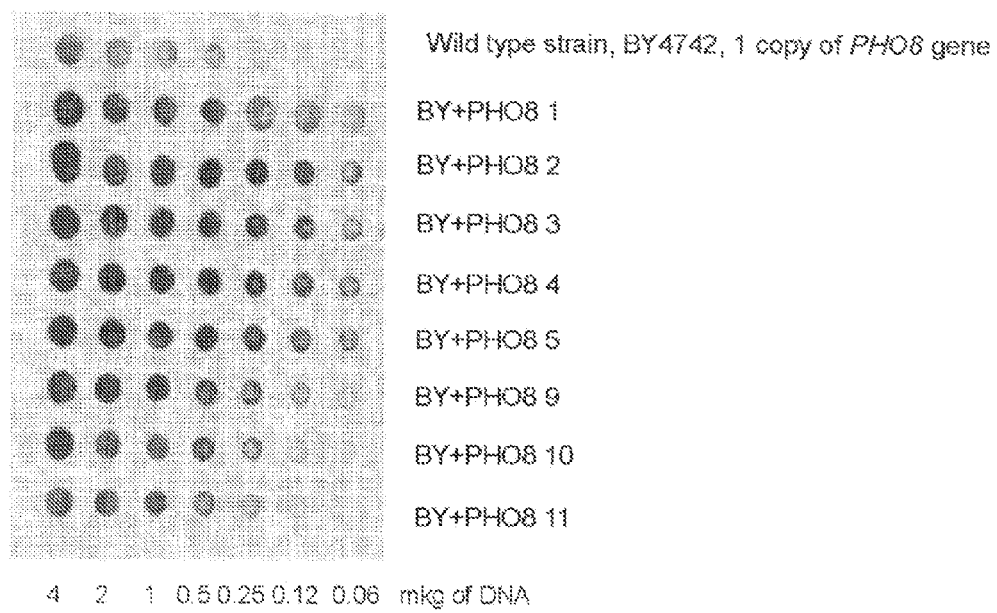
FIG. 4. Estimation of integrated expression cassette copy number by dot-blot hybridization. The top row shows wild type strain, BY4742, 1 copy of PHO8, the remaining rows show recombinant strains containing vector pUC57-delta1_2-ADHpr-PHO8-CYCt-kanMX. From 2 to 8-10 copies of PHO8 gene in the genome.

Genomic DNA preparations isolated from the recombinant strains, was subjected to dot-blot hybridization to estimate plasmid copy number which harbour the target gene, integrated into the genome. Gene PHO8 was used as a probe (FIG. 4). It was revealed that recombinant strains contained from 1 to 7-9 additional copies of PHO8 gene. A good correlation between copies number of PHO8 gene and specific alkaline phospatase activity was observed.

Figure 5:
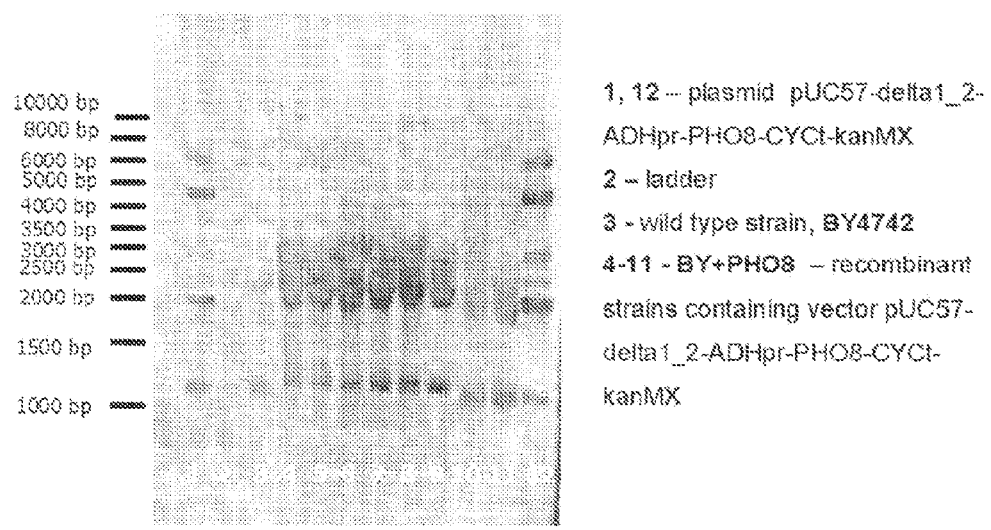
FIG. 5. Analysis of expression cassette integration pattern. A) Southern hybridization. PHO8 gene was used as a probe. HindIII was used for genomic DNA restriction B) "head-to-tale" conformation of vector integration.
Figure 5:
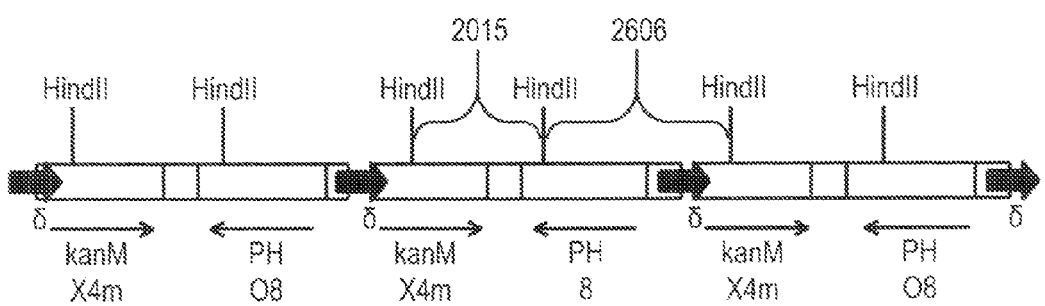

The Southern-hybridization was performed to analyse the vector Integration pattern of the tested strains (FIG. 5, A). Total genomic DNA from WT and recombinant strains were HindIII digested and hybridized with a labelled PHO8 gene. It was shown that constructed δ sequences-based vector provide tandem multi-copy integration in up to three sites of yeast genomic DNA in so called "head-to-tale" conformation (FIG. 5, B), which is consistent with published results (Lee and Da Silva, 1997).

Figure 6:
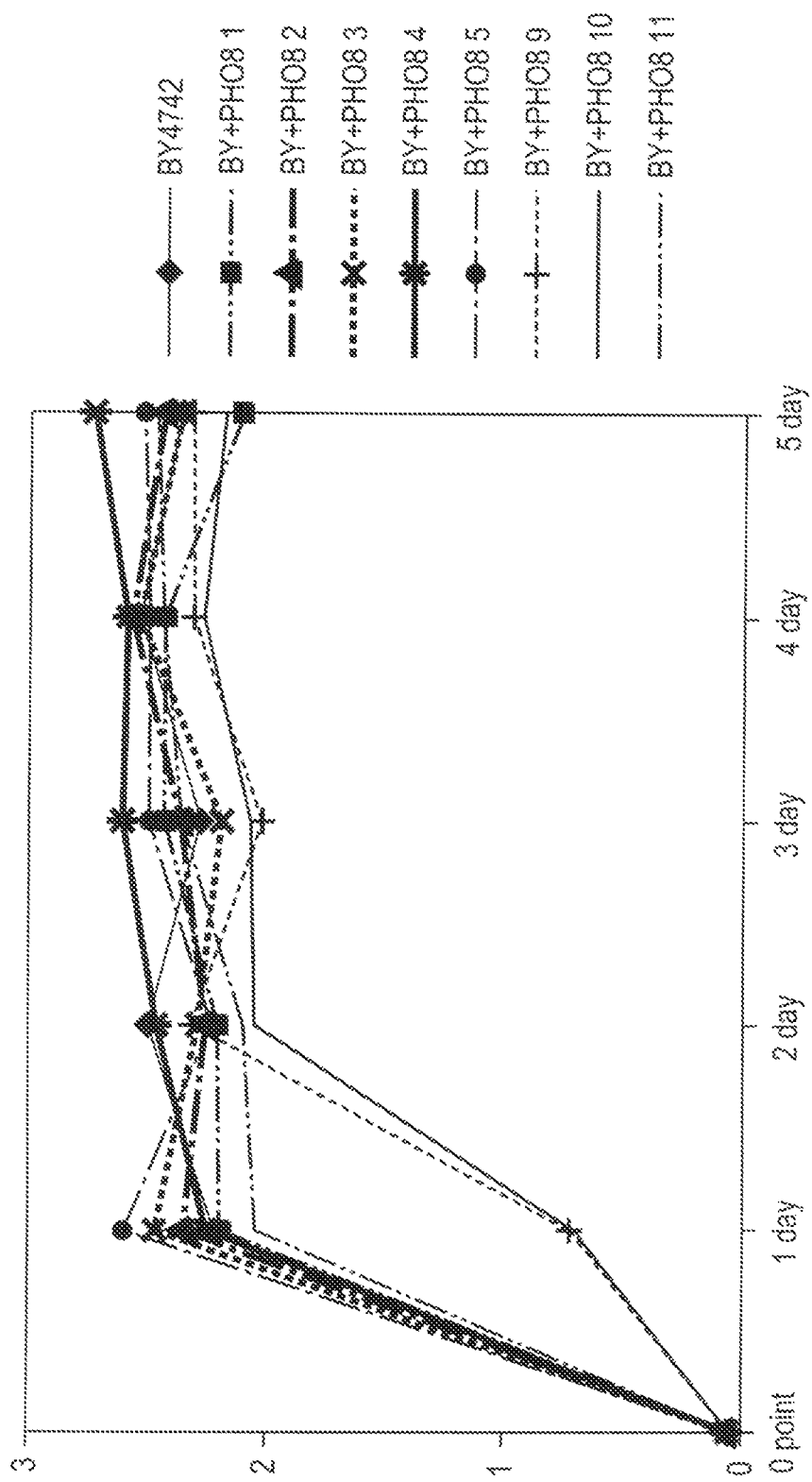
FIG. 6. Growth kinetic of strains bearing plasmid pUC57-delta1_2-ADHpr-PHO8-CYCt-kanMX. BY4742—recipient strain.

Surprisingly, several of the selected recombinant strains revealed impaired biomass accumulation, which does not correlate with the increased alkaline phosphatise activity level (FIG. 6).

Figure 7:
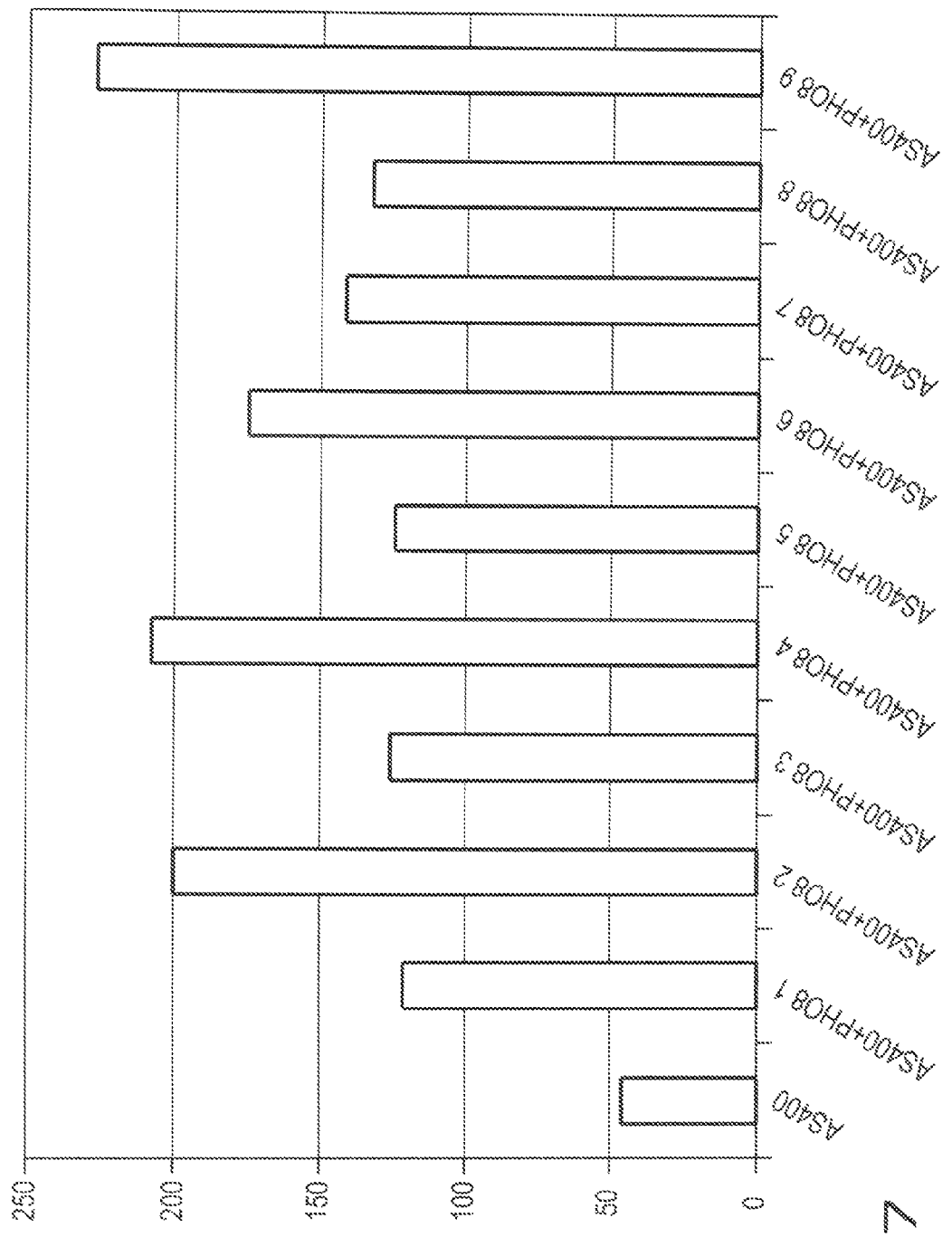
FIG. 7. Specific alkaline phosphatase activity (in nmoles of product/mg of prot.*min) of recombinant strains bearing vector pUC57-delta1_2-ADHpr-PHO8-CYCt-kanMX. AS400—recipient strain.
Figure 8:
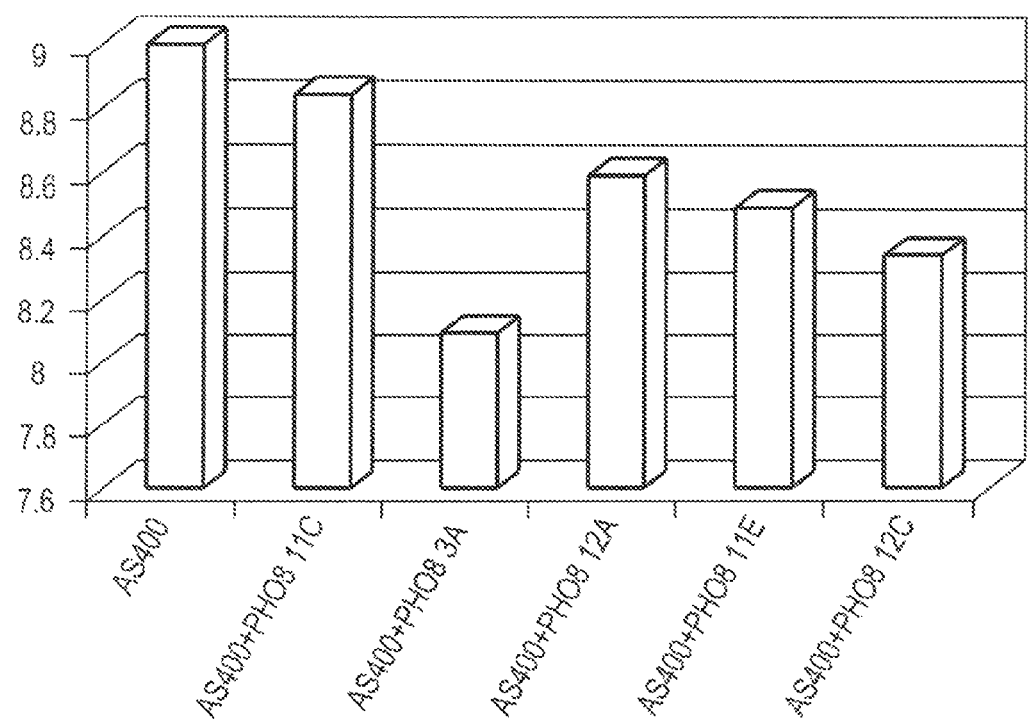
FIG. 8. ATP level (in μmoles of ATP/mg dry cell weight) in the cells of strains harbouring vector pUC57-delta1_2-ADHpr-PHO8-CYCt-kanMX. AS400—recipient strain.

The plasmid pUC57-delta1_2-ADHpr-PHO8-CYCt-kanMX was used for transformation of industrial strain AS400. Selected transformants possess at the most 5.5-fold increase of specific activity of alkaline phospatase as compared with parental strain AS400 (FIG. 7). Recombinant strains with the highest specific activity of alkaline phospatase were subjected to tested for the efficiency of alcoholic fermentation on a CSL medium supplemented with hydrolyzed corn meal. Strains AS400+-PHO8-6, AS400+PHO8-8, AS400+PHO8-3B, AS400+PHO8-12 produced increased amount of ethanol (84.4, 86.5, 84.4, 90.1 g/L) as compared with the parental strain (79.1 g/L) (Table 1). Some of the analyzed recombinant strains possessed slightly lower intracellular ATP level than that of wild type strain AS400 (FIG. 8).

TABLE 1

Ethanol synthesis of S. cerevisiae recombinant strains with derepressed PHO8 (alkaline phospatase) and initial strain AS400 on the first day of alcoholic fermentation on CSL medium supplemented with hydrolyzed corn flour.

| Strain | Ethanol 1 | Ethanol 2 | Ethanol 3 | Ethanol 4 | Ethanol (average of 4 exps) g/L | % of increase in ethanol synthesis |
|---|---|---|---|---|---|---|
| AS400 (WT) | 81.3 | 78.3 | 79.6 | 77.3 | 79.1 | — |
| AS400 + PHO8-6 | 84.8 | 81.7 | 87.3 | 83.7 | 84.4 | +6.1 |
| AS400 + PHO8-8 | 88.0 | 84.1 | 89.3 | 84.6 | 86.5 | +9.4 |
| AS400 + PHO8-3B | 85.5 | 81.6 | 88.0 | 82.3 | 84.4 | +6.7 |
| AS400 + PHO8-12 | 89.2 | 85.2 | 102.0 | 83.8 | 90.1 | +13.9 |

Cloning and Overexpression of Truncated Forms of Alkaline Phosphatase.

As described herein, some of the recombinant strains bearing plasmid pUC57-delta1_2-ADHpr-PHO8-CYCt-kanMX had up to 30 fold increase in alkaline phosphatase activity, but their growth level did not differ substantially from that of the WT strain. This result can be explained by the vacuolar localization of the alkaline phosphatase that may hinder ATP hydrolysis. In order to test we decided to construct strains containing gene encoding truncated version of alkaline phosphatase that will remain in the cytoplasm instead of being delivered to the vacuole. However there are several drawbacks that prevent that obstruct the generation of an active cytosolic form of alkaline phosphatase. First, it was shown that alkaline phosphatase is synthesized as an inactive precursor containing a C-terminal propeptide that is afterwards cleaved from the protein in vacuole in a PEP4-dependent manner (Klionsky D. and Emr S. D. 1989). During vacuolar delivery, which shares the same early stages with the secretory pathway, the precursor form of this enzyme is glycosylated in the endoplasmic reticulum. It has also been shown that the active form of alkaline phosphatase receives its metal cofactor zinc in the vacuole rather than in earlier compartments of the secretory pathway (Qiao W. et al. 1985). To estimate how these factors influence this enzyme's activity, we decided to produce several truncated forms of alkaline phosphatase. The first form lacks 60 initial amino acids that are responsible for transmembrane protein delivery; and 22 terminal amino acids, that composite the C-terminal propeptide that is normally cleaved from the protein in the vacuole. The second form has an extracellular export signal from mating pheromone a-factor (MF1α) instead of its natural delivery signal, and, finally, the third form constructed has an extracellular export signal from acid phosphatase (gene PHO5).

The DNA fragments containing the expression cassette of three mentioned PHO8 modified forms in part with selective marker flanked by δ sequences were used to transform *S. cerevisiae* strain BY4742. The presence of these expression cassettes was confirmed after transformation by PCR.

Figure 9A:
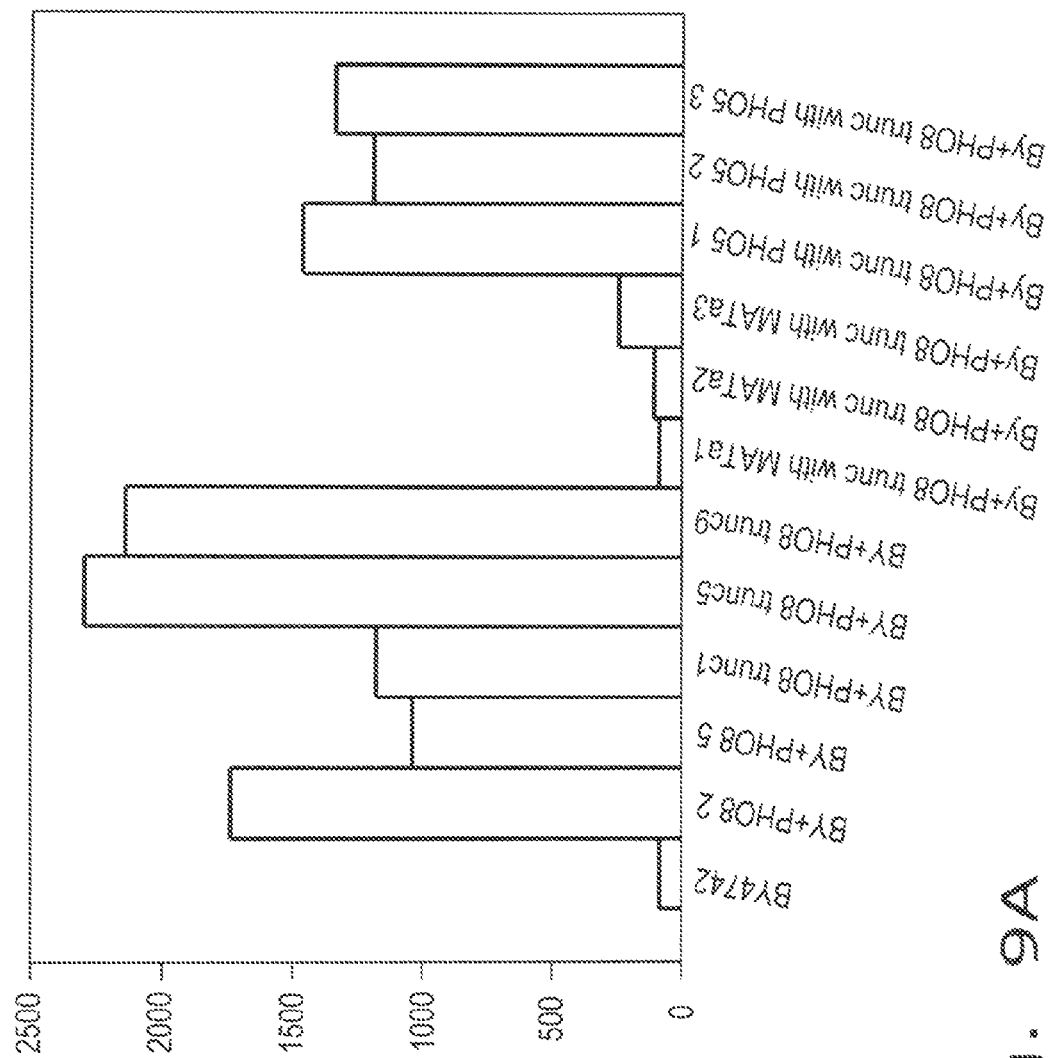
FIG. 9. Specific alkaline phosphatase activity in nmoles of product/mg of prot.*min. BY4742—WT, recipient strain. BY+PHO8 2; 5—strains containing vector pUC57-delta1_2-ADHpr-PHO8-CYCt-kanMX. BY+PHO8 trunc1; 5; 9—strains containing vector pUC57-delta1_2-ADHpr-PHO8_trunc-CYCt-kanMX. BY+PHO8 trunc with MATa 1; 2; 3—strains containing vector pUC57-delta1_2-ADHpr-MATαsign.-PHO8_trunc-CYCt-kanMX. BY+PHO8 trunc with PHO5 1; 2; 3—strains containing vector pUC57-delta1_2-ADHpr-PHO5sign.-PHO8_trunc-CYCt-kanMX. A—1 day of cultivation; B—2 days of cultivation.
Figure 9B:
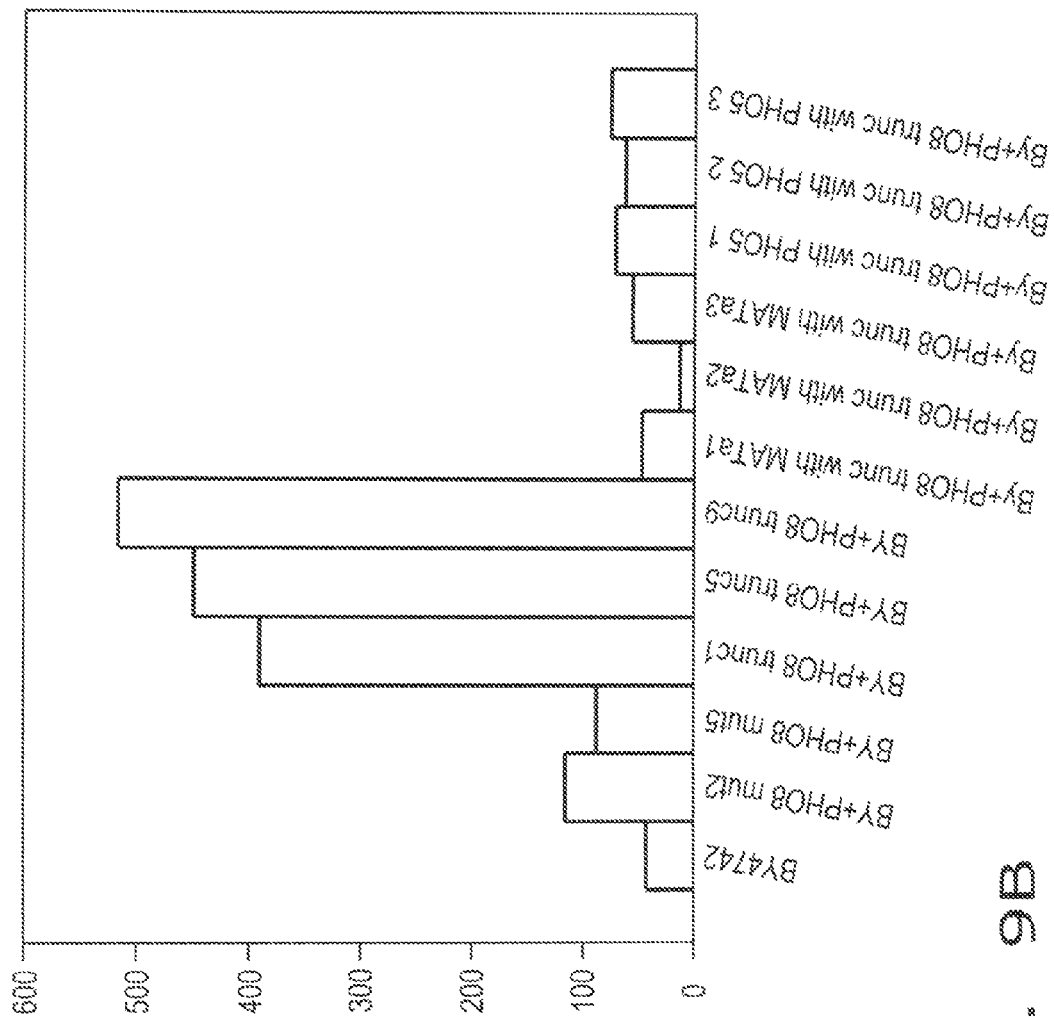

The specific alkaline phosphatase activity of the obtained recombinant strains was assayed and compared with the activity of transformants with intact form of PHO8. The intracellular alkaline phosphatase activity in strains containing plasmid pUC57-delta1_2-ADHpr-PHO8_trunc-CYCt-kanMX was at the same level as in strains with intact form of PHO8. Intracellular alkaline phosphatase activity in strains containing plasmid pUC57-delta1_2-ADHpr-MATαsign.-PHO8_trunc-CYCt-kanMX was very low, almost in the same level as in WT strain. Most likely this form of alkaline phosphatase is secreted from the cells. The intracellular alkaline phosphatase activity of strains containing plasmid pUC57-delta1_2-ADHpr-PHO5sign.-PHO8_trunc-CYCt-kanMX was high on the first day of cultivation. This activity decreased on the second day of cultivation and this can be explained by the delay in the export of the secreted form of alkaline phosphatase. (FIG. 9 A, B).

Figure 10:
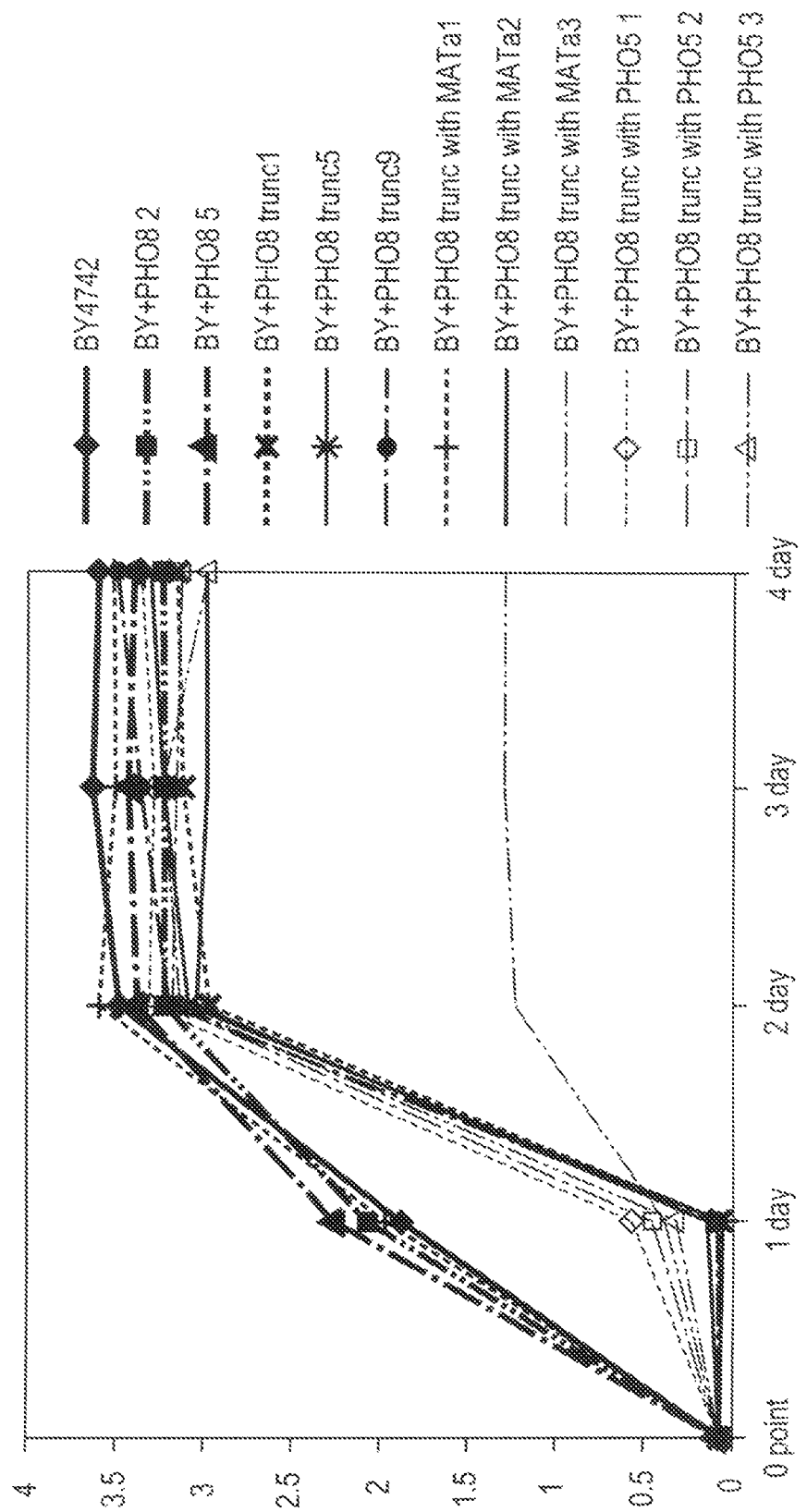
FIG. 10. Growth kinetics of the wild type strain BY4742 and its derivatives containing expression cassettes for intact (BY+PHO8 2;5) or modified (BY+PHO8 trunc1; 5; 9; BY+PHO8 trunc with MATa 1; 2; 3; BY+PHO8 trunc with PHO5 1; 2; 3) forms of PHO8 gene.
Figure 11:
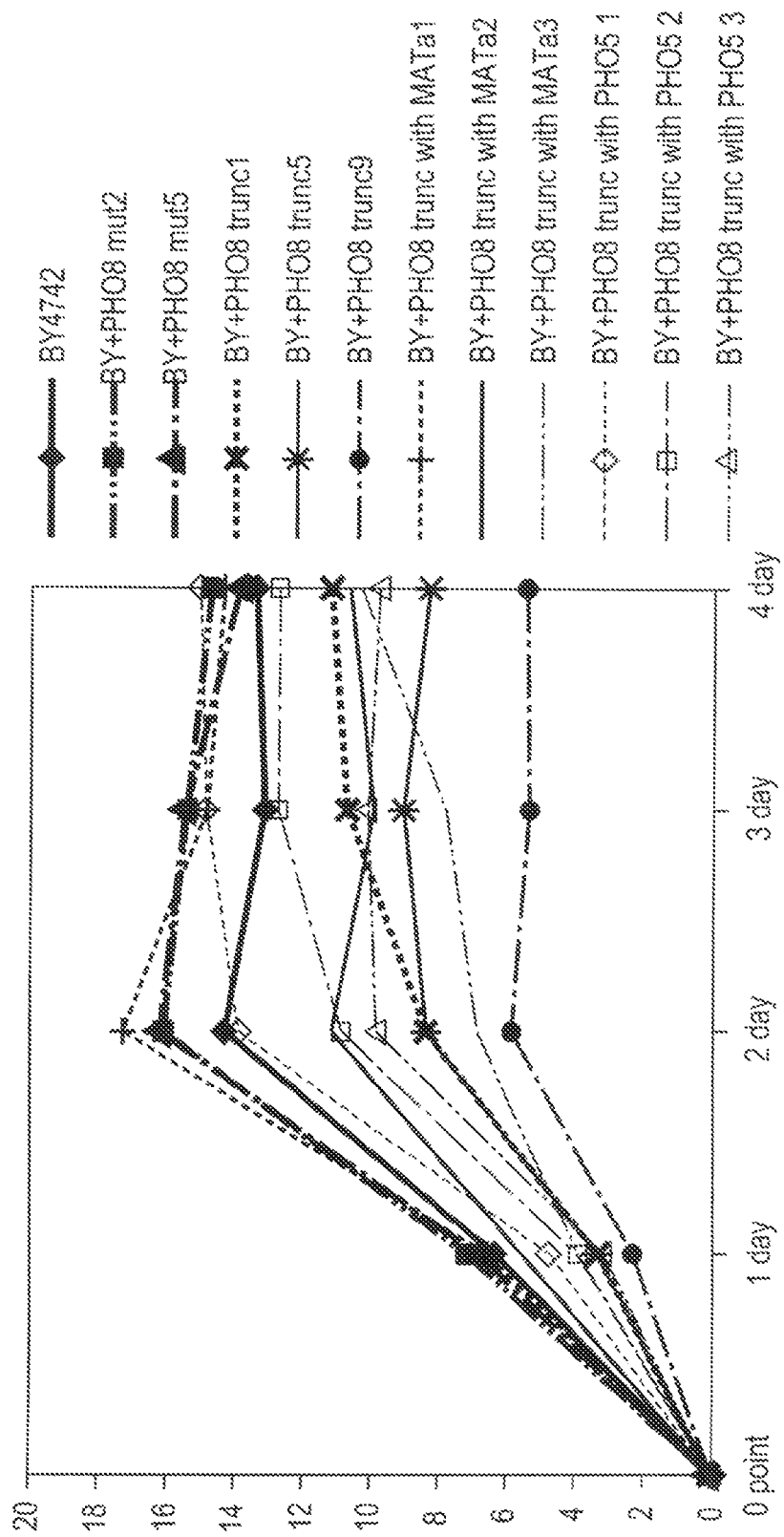
FIG. 11. Ethanol yield (in g of ethanol/g of biomass) during alcoholic fermentation by wild type strain BY4742 and its derivatives containing expression cassettes for intact (BY+PHO8 2; 5) or modified (BY+PHO8 trunc1; 5; 9; BY-PHO8 trunc with MATa 1; 2; 3; BY+PHO8 trunc with PHO5 1; 2; 3) forms of PHO8 gene.

Growth kinetics of the constructed recombinants was tested. Almost all strains with different truncated PHO8 forms had impaired growth on the first and, to a lesser degree by the second day of cultivation (FIG. 10) These recombinant strains especially those that had a truncated form of alkaline phosphatase that remains in the cell's cytoplasm produced significantly less ethanol, also (FIG. 11). This indicates that the cytosolic form of alkaline phosphatase also strongly influences the level of other cellular phosphorylated compounds, that affect all of the metabolic pathways, in particular, the reactions responsible for alcoholic fermentation.

In conclusion and on the basis of this work, the intact vacuolar form of alkaline phosphatase is suitable for achieving higher ethanol in *S. cerevisiae* cells.

REFERENCES

Ano Y., Hattori T., Kato N., Sakai Y. (2005) Intracellular ATP correlates with mode of pexophagy in *Pichia pastoris*. Biosci. Biotechnol. Biochem. 69(8): 1527-1533

Bai F. W., Anderson W. A., Moo-Young M. (2008) Ethanol fermentation technologies from sugar and starch feedstocks. Biotechnology Advances 26:89-105.

Entian K.-D., Droll L., Mecke D. (1983) Studies on rapid reversible and non-reversible inactivation of fructose-1,6-bisphosphate and malate dehydrogenase in Wild-type and glycolytic block mutants of *Saccharomyces cerevisiae*. Arch. Microbiol. 134: 187-192.

Giaever G., Chu A. M., Ni L., Connelly C., Riles L., Veronneau S., Dow S., Lucau-Danila A., Anderson K., André B., Arkin A. P., Astromoff A., El-Bakkoury M., Bangham R., Benito R., Brachat S., Campanaro S., Curtiss M., Davis K., Deutschbauer A., Entian K. D., Flaherty P., Foury F., Garfinkel D. J., Gerstein M., Gotte D., Güldener U., Hegemann J. H., Hempel S., Herman Z., Jaramillo D. F., Kelly D. E., Kelly S. L., Kotter P., LaBonte D., Lamb D. C., Lan N., Liang H., Liao H., Liu L., Luo C., Lussier M., Mao R., Menard. P., Ooi S. L., Revuelta J. L., Roberts C. J., Rose M., Ross-Macdonald P., Scherens B., Schimmack G., Shafer B., Shoemaker D. D., Sookhai-Mahadeo S., Storms R. K., Strathern J. N., Valle G., Voet M., Volckaert G., Wang C. Y., Ward T. R., Wilhelmy J., Winzeler E. A., Yang Y., Yen G., Youngman E., Yu K., Bussey H., Boeke J. D., Snyder M., Philippsen P., Davis R. W., Johnston M. (2002) Functional profiling of the *Saccharomyces cerevisiae* genome. Nature 418: 387-391.

Gonchar M. V. (1998) Sensitive method for quantitative determination of hydrogen peroxide and oxidase substrates in biological samples. Ukr. Biokhim. Zh. 70:157-163.

Gonchar M. V., Maidan M. M., Pavlishko H. M., Sibirny A. A. (2001) A new oxidase-peroxidase kit for ethanol assays in alcoholic beverages. Food Technol. Biotechnol. 39:37-42.

Hahn-Hagerdal B., Karhumaa K., Jeppsson M., Gorwa-Grauslund M. F. (2007) Metabolic Engineering for Pentose Utilization in *Saccharomyces cerevisiae*. Adv. Biochem. Engin. Biotechnol. 108:147-177.

Ingledew W. M. Alcohol production by *Saccharomyces cerevisiae*: a yeast primer, in the alcohol textbook. 3rd ed. UK: Nottingham University Press; 1999.

Jeffries T. W. (2005) Ethanol fermentation on the move. Nature 23:40-41.

Jeffries T. W., Jin Y.-S. (2004) Metabolic engineering for improved fermentation of pentoses by yeasts. Appl. Microbiol. Biotechnol. 63: 495-509.

Kaneko Y., Akio Toh-E, Oshima Y. (1982) Identification of the Genetic Locus for the Structural Gene and a New Regulatory Gene for the Synthesis of Repressible Alkaline Phosphatase in *Saccharomyces cerevisiae*. Molecular And Cellular Biology, 2(2):127-137.

Klionsky D. and Emr S. D. (1989) Membrane protein sorting: biosynthesis, transport and processing of yeast vacuolar alkaline phosphatase. The EMBO Journal 8 (8): 2241-2250.

Lancashire W. E., Dickinson J. R., Malloch R. A. (1998) DNA encoding enzymes of the glycolytic pathway for use in alcohol producing yeast. U.S. Pat. No. 5,786,186.

Lee F. W. F., Da Silva N. A. (1997) Improved efficiency and stability of multiple cloned gene insertions at the δ sequences of *Saccharomyces cerevisiae*. Appl Microbiol Biotechnol 48: 339-345.

Leskovac, V., Trivic S., Peric D. (2002) The three zinc-containing alcohol dehydrogenases from baker's yeast, *Saccharomyces cerevisiae*. FEMS Yeast Res., 2:481-494.

Panesar P. S., Marwaha S. S., Kennedy J. F. (2006) *Zymomonas mobilis*: an alternative ethanol producer. J. Chem. Technol. Biotechnol. 81:623-635.

Qiao W., Ellis C., Steffen J., Wu J.-Y., Eide D. (1985) Zinc status and vacuolar zinc transporters control alkaline phosphatase accumulation and activity in *Saccharomyces cerevisiae*. Molecular And Cellular Biology 5 (1): 248-252.

Sambrook J. and Russell D. W. (2001) Molecular cloning: a laboratory manual. 3rd edition. Cold Spring Harbor Laboratory Press, Cold Spring Harbor, N.Y.

Schubert C. (2006) Can biofuels finally take center stage? Nature Biotechnol. 24:777-784.

Sibirny A A, Semkiv M V, Dmytruk K. V. (2010) Improvement of ethanol yield and reduction of biomass accumulation in the recombinant strain of *Saccharomyces cerevisiae* overexpressing ATP degrading the enzyme//International patent WO2010/151866 A2, Dec. 29, 2010.

Sibirny A A, Abbas C A, Dmytruk K V, Kurylenko O O, Semkiv M V. (2011) Screening for *Saccharomyces cerevisiae* promoters induced under conditions of alcoholic fermentation. Draft of US Patent Application.

Sprenger G. A. (1996) Carbohydrate metabolism in *Zymomonas mobilis*: a catabolic highway with some scenic routes. FEMS Microbiol. Lett. 145:301-307.

Taxis C, Knop M. System of centromeric, episomal, and integrative vectors based on drug resistance markers for *Saccharomyces cerevisiae* BioTechniques 2006, 40:73-78.

What is claimed is:

1. A strain of *S. cerevisiae* comprising:
a nucleic acid sequence of gene PHO8 encoding for an alkaline phosphatase enzyme operably linked to a heterologous promoter that provides overexpression of the alkaline phosphatase enzyme in a cell, such that the cell has a lower intracellular ATP level present, lower biomass accumulation, and greater ethanol production is expressed at a level at least 5% greater than in an unmodified strain of *S. cerevisiae*;
wherein the alkaline phosphatase enzyme contains a vacuolar targeting sequence and the alkaline phosphatase is present in the vacuole of the cell;
wherein the nucleic acid sequence encoding the alkaline phosphatase enzyme in integrated into a genome of the cell.

2. The strain of claim 1, wherein the cell contains multiple copies of the nucleic acid sequence encoding the alkaline phosphatase enzyme is operably linked to a promoter that expresses the alkaline phosphatase enzyme in the cell.

3. The strain of claim 1, wherein the heterologous promoter is an ethanol inducible promoter from *S. cerevisiae*.

4. The strain of claim 3, wherein the inducible promoter is an alcohol dehydrogenase promoter.

5. The strain of claim 1, further characterized by producing a higher titer of ethanol during an anaerobic fermentation period than a parent strain lacking the nucleic acid sequence encoding the alkaline phosphatase enzyme operably linked to a promoter that expresses the alkaline phosphatase enzyme.

6. A method of producing ethanol comprising growing the *S. cerevisiae* according to claim 1 under anaerobic growth conditions for a time sufficient to produce ethanol.

7. A method of producing ethanol comprising:
growing a *S. cerevisiae* strain under anaerobic growth conditions for a time sufficient to produce ethanol;
wherein the *S. cerevisiae* strain comprises a nucleic acid sequence of gene PHO8 encoding for an alkaline phosphatase enzyme operably linked to a heterologous promoter that provides overexpression of the alkaline phosphatase enzyme in a cell, such that the cell has a lower intracellular ATP level present, lower biomass accumulation, and greater ethanol production is expressed at a level at least 5% greater than in an unmodified strain of *S. cerevisiae*;
wherein the alkaline phosphatase enzyme contains a vacuolar targeting sequence and the alkaline phosphatase is present in the vacuole of the cell.

8. The method of claim 7, wherein the heterologous promoter is an ethanol inducible promoter from *S. cerevisiae*.

9. The method of claim 8, wherein the inducible promoter is an alcohol dehydrogenase promoter.

\* \* \* \* \*